United States Patent [19]

Huc et al.

[11] Patent Number: 5,622,656
[45] Date of Patent: Apr. 22, 1997

[54] PROCESS OF MANUFACTURE OF BIODEGRADABLE MICROCAPSULES HAVING WALLS COMPOSED OF CROSSLINKED ATELOCOLLAGEN AND POLYHOLOSIDES

[75] Inventors: Alain Huc, Ste Foy les Lyon; Marie-Christine Levy, Reims; Chantal Buffevant, Vernaison; Marie-Christine Andry, Dizy, all of France

[73] Assignee: Societe Anonyme: Bioetica, Lyons, France

[21] Appl. No.: 328,903

[22] Filed: Oct. 25, 1994

Related U.S. Application Data

[62] Division of Ser. No. 74,701, Jun. 8, 1993, Pat. No. 5,395,620, which is a continuation of Ser. No. 749,909, Aug. 26, 1991, abandoned, which is a continuation-in-part of Ser. No. 336,711, Apr. 12, 1989, abandoned.

[30] Foreign Application Priority Data

Jan. 31, 1989 [FR] France .................... 89 01221

[51] Int. Cl.⁶ .............................. B01J 13/16; A61K 9/52
[52] U.S. Cl. .............................. 264/4.7; 264/4; 264/4.3; 264/4.32; 424/499; 426/98; 426/534; 514/963
[58] Field of Search .............................. 264/4.3, 4.32, 264/4.7, 4; 427/213.33, 213.34, 213.35, 2.14, 2.21; 424/499; 514/963; 426/98, 534

[56] References Cited

U.S. PATENT DOCUMENTS

| | | | |
|---|---|---|---|
| 3,423,489 | 1/1969 | Arens et al. | 264/4 |
| 4,280,954 | 7/1981 | Yannas et al. | 530/356 |
| 4,378,017 | 3/1983 | Kosugi et al. | 424/499 |
| 4,391,909 | 7/1983 | Lim | 435/178 |
| 4,426,337 | 1/1984 | Suzuki et al. | 264/4 |
| 4,711,783 | 12/1987 | Huc et al. | 424/460 |
| 4,780,321 | 10/1988 | Levy et al. | 424/499 |
| 4,925,677 | 5/1990 | Feijen | 424/499 X |
| 4,931,546 | 6/1990 | Tardy et al. | 530/356 |
| 5,011,692 | 4/1991 | Fujioka | 424/484 |
| 5,169,631 | 12/1992 | Rase | 424/451 |
| 5,385,738 | 1/1995 | Yamahira et al. | 424/499 X |
| 5,395,620 | 3/1995 | Huc et al. | 424/499 |

FOREIGN PATENT DOCUMENTS

| | | |
|---|---|---|
| 0268421 | 5/1988 | European Pat. Off. . |
| 0273823 | 7/1988 | European Pat. Off. . |
| 2267150 | 11/1975 | France . |
| 64-22254 | 1/1989 | Japan . |

OTHER PUBLICATIONS

"Utilising Collagen in Drug Formulation", Manufacturing Chemist. vol. 57, No. 9, Sep. 1986, pp. 64–65, 67, London, Great Britain.

"Alkohol, Glykosaminoglykane, Kollagen: Neue Anwendungen in der Kosmetik", Seifen, Ole, Fette, Wachse, vol. III, No. 1, Jan. 1985, pp. 14–16, Augsburg, Germany.

Primary Examiner—Richard D. Lovering
Attorney, Agent, or Firm—Weingarten, Schurgin, Gagnebin & Hayes LLP

[57] ABSTRACT

The invention relates to microcapsules with a mixed wall of crosslinked atelocollagen and polyholosides, for example glycosaminoglycans, and to processes for the manufacture of the said microcapsules.

According to the invention, the microcapsules comprise a mixed wall of crosslinked atelocollagen and polyholosides, for example glycosaminoglycans, the proportion of polyholosides, for example glycosaminoglycans, relative to the atelocollagen preferably being between 18 and 50% by weight. These microcapsules can be manufactured either by a process involving interfacial crosslinking or by the extrusion of a laminar flow which is broken up by vibrations into individual droplets, which fall into a crosslinking bath.

These microcapsules are biocompatible by virtue of the presence of atelocollagen, which has most of the advantageous properties of collagen, namely a very low antigenicity and a perfect biodegradability. The are therefore particularly suitable for the manufacture of cosmetic, pharmaceutical or food compositions.

25 Claims, 1 Drawing Sheet

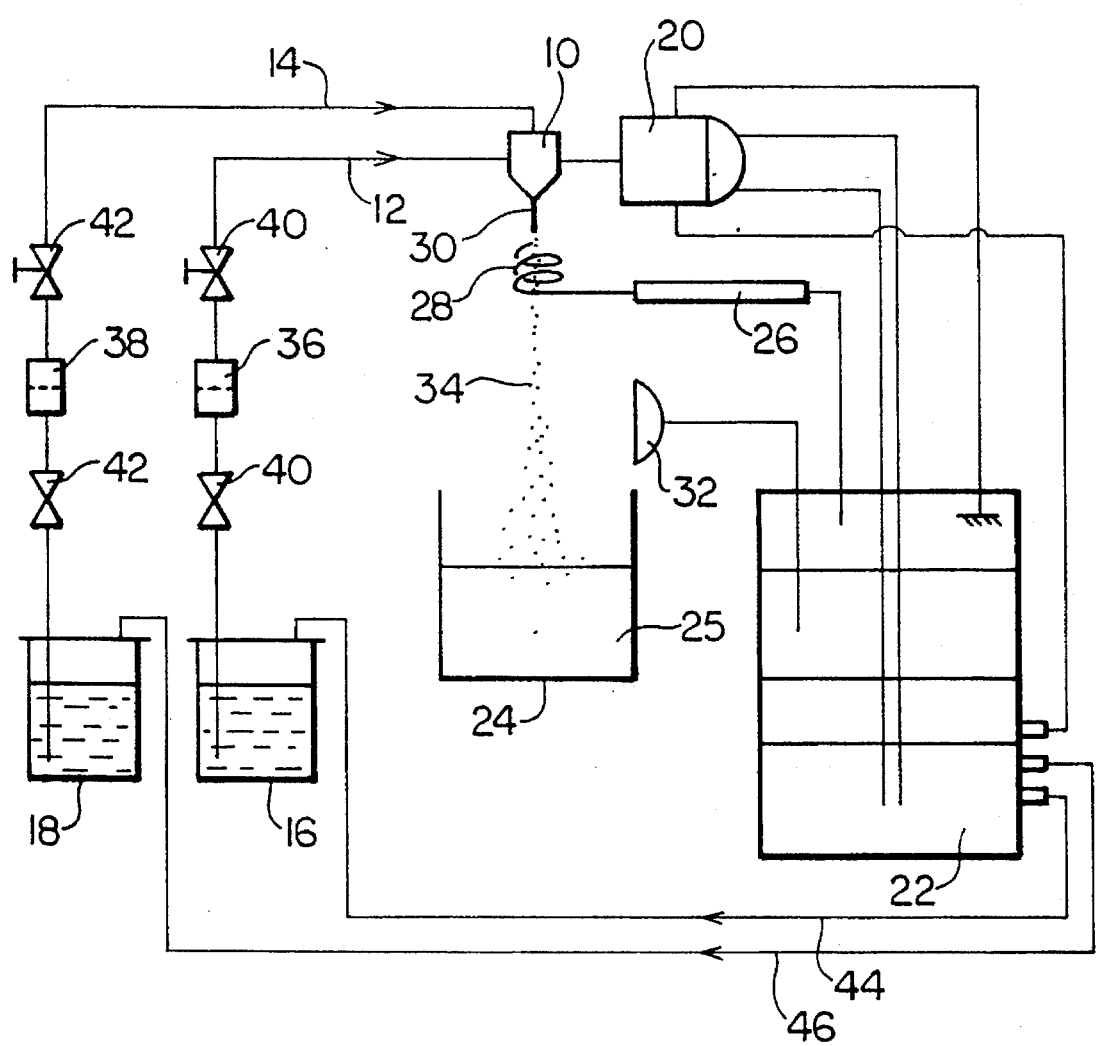
FIGURE

PROCESS OF MANUFACTURE OF BIODEGRADABLE MICROCAPSULES HAVING WALLS COMPOSED OF CROSSLINKED ATELOCOLLAGEN AND POLYHOLOSIDES

This application is a division of U.S. Pat. No. 5,395,620, filed Jun. 8, 1993, which is a FWC of Ser. No. 07/749,909, filed Aug. 26, 1991 (now abandoned), which is a continuation-in-part of Ser. No. 07/336,711, filed Apr. 12, 1989 (now abandoned).

The present invention relates essentially to the use of solutions of atelocollagen and polyholosides, for example glycosaminoglycans, for the manufacture of microcapsules, to microcapsules prepared in this way, to processes for the manufacture of these microcapsules and to cosmetic, pharmaceutical or food compositions in which they are present.

It is known that, for pharmaceutical and cosmetic applications, numerous researchers are working on the encapsulation of active substances. The following may be mentioned in particular among the desired effects of such an operation: improvement of the bioavailability, protection of the active principle in a finished formulation, protection of the active principle in the organism, especially to prevent it from degrading in the stomach, delayed release, or slow release for a sustained effect.

This encapsulation can be carried out by incorporating these active principles in microcapsules in order to introduce them into cosmetic products, pharmaceutical preparations or food products for administration by a variety of methods, such as oral and parenteral administration and application to the skin and mucosa.

In the prior art, various techniques have already been proposed for the manufacture of microcapsules with the aid of synthetic polymers. The latter substances make industrial production easy, but the microcapsules obtained are generally difficult to biodegrade and, when they are biodegradable, they give rise to degradation products which may be toxic or whose toxicity is now known.

Thus research work has been directed towards the production of microcapsules with the aid of biocompatible and biodegradable natural substances. Within this framework, researchers have used proteins. Reference may be made for example to French patent document A-2 444 497 in the name of MARS and to French patent document A-2 527 438 in the name of CNRS.

In both these documents, the technique used consists of three steps:

a) emulsification of an alkaline aqueous solution of a protein in a water-immiscible organic solvent;

b) interfacial crosslinking of the globules of the emulsion by means of a crosslinking agent, which is generally an organic acid dichloride; and finally c) isolation and washing of the resulting microcapsules by means of appropriate solvents.

In the first document the membrane consists solely of protein, whereas in the second document it is composed of a mixture of proteins and polyholosides.

Another process, known as the EXTRAMET process and carried out by the company EXTRAMET, makes it possible to obtain microcapules by using a vibrator to mechanically chop up a laminar flow produced by the extrusion of a solution of polymerizable material through a nozzle, causing the formation of globules or droplets which can then be rigidified by drying or by crosslinking in a bath containing a crosslinking agent, into which the globules or droplets fall. This technique can be applied to synthetic polymers or to proteins. The encapsulation of a water-soluble active substance in a protein capsule will be achieved by dissolution in the protein solution before extrusion. If the active substance is in the form of an oil or if it is in solution in oil, it will be encapsulated by means of coextrusion with the protein solution located outside the laminar flow.

It will be observed that there is never any mention of or allusion to the use of collagen in any of the documents of the prior art relating to the manufacture of microcapsules, and in particular in the two documents 2 444 497 and 2 527 438 cited above, although the processes are applied to proteins in general.

The inventors of the present invention attempted to use collagen in the processes described in the above documents, as well as in the EXTRAMET technique.

These experiments ended in failure because these techniques are not applicable to collagen. In fact, to achieve effective crosslinking, it is necessary to prepare solutions of collagen in a medium strongly buffered at a pH greater than or equal to 5.5.

Now, normal collagen, i.e. native collagen, precipitates partially and it is therefore very difficult to obtain homogeneous mixtures. It is not possible to prepare an emulsion with an organic liquid, so the processes described in the above French patent documents FRA-2 444 497 and FR-A-2527438 cannot be used. The same also applies to the EXTRAMET laminar extrusion technique, in which it is impossible to obtain a constant flow with a heterogeneous mixture.

One object of the present invention is therefore to solve the novel technical problem which consists in providing a solution making it possible to manufacture microcapsules whose wall comprises, at least in part, collagen or a product of the collagen type having the same properties as collagen, with the processes of the prior art.

A further object of the present invention is to solve the above-mentioned technical problem by means of extremely simple manufacturing processes which can be used on the industrial scale and which also enable the size of the microcapsules to be adjusted as desired, in particular within a range of dimensions from less than 1 to 3000 μ.

According to the present invention, it has been discovered, totally unexpectedly, that the technical problems detailed above can be solved extremely easily by using a solution of atelocollagen and polyholosides, for example glycosaminoglycans, as the starting material.

It is on the basis of this discovery, totally unexpected by those skilled in the art, that the present invention was developed, representing a decisive technical advance for those skilled in the art since atelocollagen has most of the advantageous properties of collagen, namely a very low antigenicity together, of course, with a perfect biodegradability.

Thus, according to a first aspect, the present invention relates to the use of a solution of atelocollagen and polyholosides, for example glycosaminoglycans, for the manufacture of microcapsules. Preferably, these microcapsules contain an active principle, especially of the cosmetic, pharmaceutical or edible type.

According to a second aspect, the present invention relates to microcapsules which comprise a mixed wall of crosslinked atelocollagen and polyholosides, for example glycosaminoglycans.

Atelocollagen is distinguished from collagen in that the telopeptides which crosslink the collagen molecule have been selectively removed, thereby forming atelocollagen. The use of atelocollagen instead of collagen is a very important feature of the present invention. The use of atelocollagen, instead of collagen, as a component of the stabilizing support also avoids the problems associated with handling a gelling agent, such as collagen, and unwanted precipitation associated with collagen as discussed above.

The proportion of polyholosides, for example glycosaminoglycans, relative to the atelocollagen can vary from 15 to 50% by weight. These polyholosides, for example glycosaminoglycans, can advantageously be those described within the framework of the manufacturing processes described below. The same applies to the other characteristics mentioned for the process which are found in the microcapsules themselves.

According to a third aspect, the present invention further relates to a process for the manufacture of microcapsules which comprises the following successive steps:

a) a solution of atelocollagen and a solution of polyholosides, for example glycosaminoglycans, are prepared separately;

b) the solution of atelocollagen is mixed with the solution of polyholosides, for example glycosaminoglycans, so as to form a homogeneous solution of atelocollagen and polyholosides, for example glycosaminoglycans;

c) an emulsion is formed with the solution of atelocollagen and polyholosides, for example glycosaminoglycans, as the disperse phase in a hydrophobic liquid forming the continuous phase, in which the atelocollagen and/or the polyholosides, for example glycosaminoglycans, are essentially insoluble; and d) a solution of a crosslinking agent containing reactive groups capable of reacting with the acylatable groups of the atelocollagen and the polyholosides, for example glycosaminoglycans, is added to the resulting emulsion so as to cause an interfacial crosslinking reaction between the atelocollagen and the polyholosides, for example glycosaminoglycans, on the one hand, and the crosslinking agent on the other, in order to form microcapsules whose wall is a mixed wall of crosslinked atelocollagen and polyholosides, for example glycosaminoglycans.

Advantageously, the process also comprises the additional step of separation of the microcapsules by any appropriate means, especially by natural decantation after one or more washes have been carried out if necessary.

According to a fourth aspect, the present invention relates to a process for the manufacture of microcapsules containing a water-immiscible oil, which comprises the following successive steps:

a) a solution of atelocollagen and a solution of polyholosides, for example glycosaminoglycans, are prepared separately;

b) the solution of atelocollagen is mixed with the solution of polyholosides, for example glycosaminoglycans, so as to form a homogeneous solution of atelocollagen and polyholosides, for example glycosaminoglycans;

c) an emulsion is formed with the oily phase, containing a crosslinking agent, as the disperse phase in the solution of atelocollagen and polyholosides, for example glycosaminoglycans, forming the continuous phase;

d) the emulsion is agitated for the time necessary to achieve an adequate degree of interfacial crosslinking, producing microcapsules whose wall is a mixed wall of crosslinked atelocollagen and polyholosides, for example glycosaminoglycans; and e) the microcapsules are separated off by any appropriate means, especially by natural decantation after one or more washes have been carried out if necessary.

According to another aspect, the present invention also provides a process for the manufacture of microcapsules which comprises the following successive steps:

a) a solution of atelocollagen and a solution of polyholosides, for example glycosaminoglycans, are prepared separately;

b) the solution of atelocollagen is mixed with the solution of polyholosides, for example glycosaminoglycans;

c) a crosslinking bath containing an appropriate crosslinking agent is prepared;

d) laminar extrusion of the homogeneous solution of atelocollagen and polyholosides, for example glycosaminoglycans, is effected through an extrusion nozzle, the laminar flow being subjected at the same time to vibrations in order to break up the laminar flow into individual droplets;

e) the individual droplets are allowed to fall into the said crosslinking bath, giving microcapsules by crosslinking of the atelocollagen and the polyholosides, for example glycosaminoglycans; and f) the microcapsules are separated off by any appropriate means, especially by natural decantation after one or more washes have been carried out if necessary.

It will be noted that steps a) and b) above are common to steps a) and b) of the interfacial crosslinking process, so everything stated above in this respect applies to this second process involving extrusion.

According to yet another aspect, the present invention also provides a process for the manufacture of microcapsules for the encapsulation of an oily phase, which comprises the following successive steps:

a) a solution of atelocollagen and a solution of polyholosides, for example glycosaminoglycans, are prepared separately;

b) the solution of atelocollagen is mixed with the solution of polyholosides, for example glycosaminoglycans;

c) the crosslinking agent is dissolved in the oily phase to be encapsulated;

d) laminar coextrusion of the homogeneous solution of atelocollagen and polyholosides, for example glycosaminoglycans, and the oily phase to be encapsulated is effected through an extrusion nozzle, the laminar flow being subjected at the same time to vibrations in order to break up the laminar flow into individual droplets;

e) the individual droplets are allowed to fall into a stirred water bath; and f) the microcapsules are separated off by any appropriate means, especially by natural decantation after several washes with water have been carried out if necessary.

According to one advantageous characteristic of the manufacturing processes according to the invention, the crosslinking agent is an acid dichloride, an acid anhydride or a dibasic or polybasic carboxylic acid. According to a preferred characteristic, the crosslinking agent is selected from terephthaloyl chloride, phthaloyl chloride, sebacoyl chloride, succinoyl chloride, the chloride of a tricarboxylic acid such as citric acid, or an acid anhydride such as succinic anhydride.

Any of the solvents described in the above documents can be used as the hydrophobic liquid in which the atelocollagen and/or the polyholosides, for example glycosaminoglycans, are insoluble. Cyclohexane or chloroform will preferably be used.

In another modified embodiment of the processes according to the invention, the mixture of atelocollagen and polyholosides, for example glycosaminoglycans, is prepared by introducing the solution of polyholosides, for example glycosaminoglycans, into the solution of atelocollagen.

In one particular embodiment, the solution of polyholosides, for example glycosaminoglycans, is prepared by dissolving the polyholoside, for example the glycosaminoglycan, preferably obtained in the dry state, for example by having been lyophilized, in an aqueous solution whose pH is adjusted so that, after mixing with the solution of atelocollagen, the pH of the mixture is between 5.5 and 10. Preferably, the aqueous solution is a basic buffer solution. This basic buffer solution can be an aqueous solution of sodium hydroxide or, preferably, an aqueous solution of a basic buffer obtained by the neutralization of a weak acid with a strong base, such as sodium carbonate, sodium acetate or sodium citrate, or in solutions of sodium and potassium phosphates.

According to another advantageous characteristic of the processes according to the invention, the concentration of polyholosides, for example glycosaminoglycans, relative to the concentration of atelocollagen is 15 to 50% by weight.

According to another advantageous characteristic of the processes according to the invention, the concentration of polyholosides, for example glycosaminoglycans, in the solution of polyholosides, for example glycosaminoglycans, is 0.5 to 4%, preferably 0.5 to 2% and particularly preferably about 1%.

According to another characteristic of the processes of the invention, the solution of atelocollagen is an aqueous solution of atelocollagen having a concentration of between 0.5 and 2% by weight. This solution of atelocollagen can be obtained, according to the invention, by dissolving atelocollagen fibers in a slightly acidic, aqueous solution.

In one particular embodiment, these atelocollagen fibers are dissolved in 0.1M acetic acid.

In another particular embodiment of the processes according to the invention, the atelocollagen is obtained by the enzymatic digestion of collagen.

In one particular modified embodiment, the glycosaminoglycans used according to the invention are selected from structural glycosaminoglycans, which are in turn selected from the group consisting of chondroitin 4-sulfate, chondroitin 6-sulfate, dermatan sulfate, heparan sulfate and keratan sulfate, as well as heparin and its derivatives. In particular, low molecular weight heparin ranging between 2,000–10,000 mw, and heparin from cosmetically or pharmaceutically acceptable salts such as calcium and sodium salts. Another suitable polyholoside is dextran.

One or more desired active principles in the form of a solution, suspension or emulsion, in particular one or more substances of interest in cosmetics, pharmaceuticals or food, can be introduced into the aqueous solution of atelocollagen and polyholosides, for example glycosaminoglycans.

In particular, in the above-mentioned extrusion technique, it is possible to extrude the substance to be encapsulated, incorporated inside the laminar flow of atelocollagen and polyholosides, for example glycosaminoglycans, which are to form the wall of the microcapsules.

In the case where the oily phase is the encapsulated phase, one or more substances of interest in cosmetics, pharmaceuticals or food, in the form of a solution, suspension or emulsion, can be incorporated into this oily phase.

In particular, in the above-mentioned extrusion technique, it is possible to coextrude the active substance, in solution, in suspension or in emulsified form in the oily phase, inside the laminar flow of atelocollagen and polyholosides, for example glycosaminoglycans, which are to form the wall of the microcapsules.

Finally, according to a seventh aspect, the present invention further relates to a cosmetic composition or a pharmaceutical composition which comprises microcapsules with a mixed wall of crosslinked atelocollagen and polyholosides, for example glycosaminoglycans. Preferably, these microcapsules contain, at least in part, an active principle, in particular a cosmetic active principle or a pharmaceutical active principle.

Other objects, characteristics and advantages of the invention will become clear from the following explanatory description referring to several Examples of how the invention is put into practice, these Examples being given simply by way of illustration and therefore in no way limiting the scope of the invention. In the Examples, all the percentages are given by weight, unless indicated otherwise.

BRIEF DESCRIPTION OF THE DRAWING

The Figure schematically represents an apparatus for the manufacture of macrocapsules according to the invention by the EXTRAMET technique for the extrusion of a laminar flow, as described in Example 5.

EXAMPLE 1 according to the invention

In this Example, microcapsules are manufactured which have a mean diameter of 20 μm and contain a water-soluble active principle, namely vitamin C.

a) Preparation of decrosslinked collagen or atelocollagen

The skin of a freshly slaughtered calf is subjected to chemical depilation in a bath containing 3% of sodium sulfide and 4% of lime, the proportions being 100 g of skin to 200 $cm^3$ of solution. The dermis is then isolated from the rest of the skin by a slitting operation using a rotating band saw.

The tissue obtained is ground and extruded through a grid having 4 mm holes. The ground material is then brought into contact for 3 weeks with a saturated solution of line in proportions of 1 kg to 4 l of solution. This procedure selectively removes the telopeptides from collagen, thereby forming atelocollagen. The skin treated in this way is separated from the supernatant by continuous centrifugation at an acceleration of 2000 g using a centrifuge rotating at 4000 rpm. The residue is then washed twice with running water in a stainless steel vat, with slow stirring, in proportions of 1 kg to 4 l of bath. The ground material is then subjected to two treatments with phosphate buffer of pH 7.8 (21.7 g/l of $Na_2HOP_4$ and 0.78 g/l of $KH_2PO_4$) under the same conditions as for the washing with water. The residue is then washed with two baths of sterile deionized water. The ground material obtained is placed in a solution of acetic acid (0.5 g/l, pH 3.4) in proportions of 1 kg to 20 l of bath. After 5 minutes of stirring, the supernatant is separated from the residue by continuous decantation using the previous technique. The atelocollagen is then precipitated from the supernatant by the addition of dry sodium chloride in a proportion of about 10% relative to the bath. After decantation under gravity the fibers obtained are dialyzed against sterile deionized water with the aid of dialysis membranes, which preferably consist of gut with a cut-off threshold of between 6000 and 8000 daltons.

b) Preparation of chondroitin 4-sulfate

Lamb's nasal septa, from which the muscular and adipose tissues have been removed, are chipped up and ground by extrusion through a grid having 4 mm holes, the ground material is placed for 24 hours, at a temperature of 6° C., in a potassium chloride buffer (11.8 g/l of KCl, 78.8 mg/l of cysteine, 180 mg/l of EDTA) containing 1% of "MERCK" papain. The proportions are 130 g of ground material to 1 l of buffer.

The supernatant is separated from the residue by continuous centrifugation using a centrifuge rotating at 4000 rpm. 40 g/l of trichloroacetic acid are then added to the supernatant. The precipitate is removed by continuous centrifugation using the previous technique. The supernatant is neutralized with sodium hydroxide pellets. The mixture is then dialyzed against sterile deionized water using gut with a cut-off threshold of between 6000 and 8000 daltons. The dialyzed solution is lyophilized. The chondroitin 4-sulfate is obtained in the dry state.

c) Preparation of a homogeneous solution of atelocollagen and chondroitin 4-sulfate in a buffered medium of pH 9.8

The atelocollagen in the form of fibers, coming from the dialysis gut, is dissolved in a 0.1M aqueous solution of acetic acid so as to give an atelocollagen concentration of 3.2%, and the resulting solution of chondroitin 4-sulfate in which the buffer has been produced with sodium carbonate, the volume and concentration of the said solution of chondroitin 4-sulfate being such that the final concentrations in the homogeneous mixture of atelocollagen and chondroitin 4-sulfate are as follows:

—atelocollagen . . . 1.6%
—chondroitin 4-sulfate . . . 0.6%
—anhydrous sodium carbonate . . . 4.8%
—methyl parahydroxybenzoate . . . 0.4%
—deionized water . . . remainder The pH of the mixture is adjusted to 9.8 with concentrated hydrochloric acid. 2 kg of this solution are prepared.

d) Preparation of the crosslinking agent 400 g of terephthaloyl chloride are ground in a mortar. This is added to 8 l of a mixture of fatty acid esters which are commercially available under the tradename DRAGOXAT®, sold by the German company DRAGOCO. The resulting mixture is stirred with a mechanical stirrer.

e) Emulsification 300 ml of the emulsifier Span 85®, sold by ICI, and 5700 ml of cyclohexane are introduced into a cooled stainless steel vat. The whole is agitated for 10 minutes with an Ultra Turax® agitating system rotating at 7200 rpm.

The homogeneous solution of atelocollagen and chondroitin 4-sulfate, in which 0.2% of vitamin C has been dissolved, is then poured into the vat.

f) Crosslinking

The solution of crosslinking agent is added to the resulting emulsion, with continued agitation. Five minutes later, the speed of rotation of the agitator is reduced by 10% and agitation is continued for a further 25 minutes.

The microspheres obtained are separated off using a centrifuge of the Robatel® type from ROBATEL, Lyon, France, rotating at 1000 rpm.

g) Washing

The atelocollagen microcapsules obtained can be washed five times with 1500 ml of the above-mentioned mixture of fatty acid esters —Dragoxat®—and are separated from the suspension under the same conditions as previously. 1.9 kg of microcapsules are obtained; they can be suspended for example in Carbopol® or collagen gels.

EXAMPLE 2 according to the invention

Manufacture of microcapsules with a mean diameter of 400 μ, containing the insoluble pigment DC RED 30 suspended in the aqueous phase a) Preparation of a solution of atelocollagen and chondroitin 4-sulfate in a buffered medium of pH 9.8

10 kg of this solution are prepared as described in Example 1. The colorant DC RED 30, in powder form, is introduced into the stirred preparation at a concentration of 1%.

b) Preparation of the crosslinking agent 1.8 kg of terephthaloyl chloride are ground in a mortar and placed in 40 l of a mixture of fatty acid esters, namely Dragoxat®. The resulting mixture is stirred for 30 minutes.

c) Emulsification 1050 ml of the emulsifier Span 85® (ICI) and 29 l of cyclohexane are introduced into a stainless steel vat of cylindrical shape. The homogeneous solution of atelocollagen and chondroitin 4-sulfate, containing the colorant, is poured into the mixture, with mechanical agitation. The resulting mixture is agitated for a few minutes to give an emulsion.

d) Crosslinking

The solution of crosslinking agent prepared as in Example 1 is added to the agitated emulsion. Agitation is continued for 30 minutes.

The microcapsules obtained are recovered by decantation as described in Example 1.

e) Washing

Four washes can be carried out in proportions of 10 l of Dragoxat® to 10 kg of microspheres, which are recovered by natural decantation. A fifth wash is carried out with the same amount of Dragoxat® but, in this case, the microcapsules are separated from the bath by decantation using a Robatel® centrifuge rotating at 1000 rpm.

1 kg of initial solution of atelocollagen and polyholosides, for example glycosaminoglycans, gives about 900 g of microcapsules. As previously, there can be suspended for example in a Carbopol® or collagen gel.

EXAMPLE 3

Manufacture of microcapsules with a mean diameter of 50 μm, containing olive oil emulsified in the aqueous phase a) Preparation of a solution of atelocollagen and chondroitin 4-sulfate in a buffered medium of pH 9.8

2 kg of this solution are prepared as described in Example 1.

b) Preparation of the crosslinking agent 400 g of terephthaloyl chloride are incorporated into 8 l of Dragoxat® under the conditions described in Example 1.

c) Preparation of a primary emulsion of olive oil in the solution of atelocollagen and chondroitin 4-sulfate 400 ml of olive oil are emulsified in 2 kg of the lution of atelocollagen and chondroitin 4-sulfate by mechanical agitation for 3 minutes using an Ultra Turax agitating system rotating at 7500 rpm.

d) Emulsification

The primary emulsion obtained is dispersed in 6 l of a mixture prepared from 5700 ml of DRAGOXAT® and 300 ml of Span 85®, by mechanical agitation for 5 minutes using a RAYNERI® agitator rotating at 1500 rpm.

e) Crosslinking

The solution of crosslinking agent is added to the resulting emulsion, agitated as before. Agitation is continued for 30 minutes.

f) Washing

The microcapsules obtained can be washed
—twice with 1500 ml of DRAGOXAT® (cf. Example 1),
—then once with 1500 ml of 1:1 v/v ethanol/water mixture containing 1% v/v of Tween 20® emulsifier,
—and then twice with water.

2.1 kg of microcapsules are obtained.

EXAMPLE 4 according to the invention

Manufacture of microcapsules with a mean diameter of 50 µ, containing a salmon oil a) Preparation of a solution of atelocollagen and chondroitin 4-sulfate in a buffered medium of pH 9.8

9 kg of this solution are prepared as described in Example 1.

b) Preparation of salmon oil to be encapsulated 150 ml of sebacoyl chloride are dissolved in 3 l of salmon oil.

c) Emulsification and crosslinking

The 3 l of salmon oil containing the crosslinking agent are added to 9 kg of the atelocollagen/chondroitin 4-sulfate solution, mechanically agitated in a vat as described in Example 1. The emulsion is agitated for 1 hour.

d) Washing

The microcapsules recovered by natural decantation are placed in a water bath with a volume of 9 l. Four washes are carried out under the same conditions. This gives 2.8 kg of microcapsules, which can also be suspended for example in Carbopol® or collagen gels.

EXAMPLE 5 according to the invention

Manufacture of microcapsules with a mean diameter of 400 µ, containing oenethera oil a) A homogeneous solution of atelocollagen and chondroitin 4-sulfate in a buffered medium of pH 9.8 is prepared as described in Example 1. 2 kg of this homogeneous solution are prepared.

b) Preparation of the crosslinking bath 350 g of terephthaloyl chloride are dissolved in 5 l of oenethera oil. The solution is stirred for 30 minutes.

c) Coextrusion and crosslinking of the microcapsules

This is done using the Extramet apparatus represented schematically in the single Figure attached.

This apparatus comprises essentially an extrusion nozzle 10 which makes it possible to effect coextrusion by the presence of two concentric orifices fed separately by two supply lines 12, 14, which serve for example to supply the solution of atelocollagen and polyholosides, for example glycosaminoglycans, according to the invention, from a reservoir 16 and, respectively, an active principle, for example oenethera oil from an active principle reservoir 18. Associated with this nozzle 10 is a vibrating device 20 governed by control means 22. This apparatus also comprises a crosslinking bath 24 located at a distance under the nozzle 10, the said bath containing the solution of crosslinking agent 25.

This apparatus also comprises an electrode 26 with a spiral end 28 arranged concentrically with the laminar flow 30 coextruded from the nozzle 10, so as to separate the droplets generated by the vibrator 20 in order to avoid coalescence of these droplets. Provision can also be made for a flash stroboscope 32 so that the droplets generated in this way can be observed visually as they fall into the crosslinking bath 25.

The flow rate of the homogeneous solution of atelocollagen and polyholosides, for example glycosaminoglycans, present in the reservoir 16 is the same as that of the oenethera oil present in the reservoir 18, constituting the active principle, and is 800 ml/h. The frequency of vibration of the vibrator 20 is 125 kHz.

The droplets 34 generated by the vibrator 20 from the laminar flow produced in the coextrusion nozzle 10 are received in 1 l of crosslinking bath 25, stirred by means of a magnetic bar. The bath is renewed every 30 minutes.

Filters 36, 38 and valves 40, 42 can be provided, in conventional manner, on the lines 12, 14 for supplying the nozzle 10. The various liquids can be conveyed through the lines 12, 14 by placing the reservoirs 16, 18 under pressure by means of appropriate supply lines 44, 46.

d) Washing

The microcapsules obtained by crosslinking of the droplets in the crosslinking bath 25 are washed five times with a 1% aqueous solution of sodium dodecylsulfate and recovered by natural decantation between successive washes as described in Example 1. After this treatment, the microcapsules are recovered by flotation.

1 kg of the solution of atelocollagen and polyholosides, for example glycosaminoglycans, makes it possible to obtain about 1.300 kg of microspheres containing oenethera oil.

Microcapsules with a mean diameter of 300 µm or more can be used to protect cosmetic active principles in a finished product. It is possible to achieve immediate breaking of the microcapsules on the surface of the skin, with which the membranes integrate perfectly to give a very good cosmetic feel.

Microcapsules with a mean diameter of 50 µm, as obtained in example 1, are easily integrated into the stratum corneum, from which the active principle is released.

These microcapsules can be colored with insoluble pigments, giving a pleasant and novel visual appearance.

EXAMPLE 6 according to the invention

Manufacture of microcapsules with a mean diameter of 400 µ, containing salmon oil a) Preparation of a homogeneous solution of atelocollagen and chondroitin 4-sulfate in a buffered medium of pH 9.8

2 kg of this homogeneous solution are prepared as described in Example 1.

b) Preparation of salmon oil to be encapsulated 100 ml of sebacoyl chloride are dissolved in 2 l of salmon oil.

c) Coextrusion and crosslinking of the microcapsules

Coextrusion and crosslinking of the microcapsules are effected under the same conditions as those described in Example 5, except for the flow rates, which are 1.2 l/h for the homogeneous solution of atelocollagen and chondroitin 4-sulfate and 1 l/h for the salmon oil In this modified embodiment, there is no longer a crosslinking bath, crosslinking having taken place during coextrusion and formation of the droplets.

d) Reception and washing of the microcapsules

The microcapsules are received in a stirred 5 l water bath. The microcapsules are washed four times with the same bath and recovered by decantation. 2 kg of microcapsules are obtained.

EXAMPLE 7 according to the invention

Manufacture of microcapsules of a means diameter of 400 μm containing vitamine C, from a homogeneous mixture of atelocollagen and dextran.

a) Atelocollagen is prepared according to the procedure described in Example 1 b) Preparation of dextran

Dextran is obtained by lyophilisation from Rheomacrodex®, a dextran product sold by SYNTHELABO - 58, rue Glacière - Paris 13ème - FRANCE. To obtain 10 g of dextran, it is necessary to weight 109 g of Rheomacrodex.

c) Preparation of an homogeneous solution of atelocollagen and dextran in a buffer medium of pH 9.8

The procedure described in Example 1 under c), page 12, is followed except that the basic aqueous buffer solution of dextran is used in place of that of chondroitin 4-sulfate and there is obtained the following mixture:

—atelocollagen . . . 1.6%
—dextran . . . 0.6%
—anhydrous sodium carbonate 4.8%
—methyl parahydroxybenzoate 0.4%
—deionized water . . . remainder The pH of the mixture is adjusted to 9.8 with concentrated hydrochloric acid. 2 kg of this solution are prepared.

d) Preparation of the crosslinking agent

The crosslinking agent is prepared as described under d) in Example 1, page 13.

e) Emulsification 210 ml of emulsifier Span 85® sold by ICI and 5,790 ml of cyclohexane are introduced into a cooled stainless steel vat. The whole is mechanically agitated during 10 minutes with a planetary agitating system at 100 rpm.

The homogeneous solution of atelocollagen and dextran, in which 0.2% of vitamin C has been solved, is poured into the vat.

f) Crosslinking

The solution of crosslinking agent is added to the resulting emulsion, with continued agitation. Five minutes later, the speed of rotation of the agitator is reduced by 10% and agitation is continued for a further 25 minutes.

The microspheres obtained are separated off using a centrifuger of the Robatel type from ROBATEL, Lyon, France, rotating at 1000 rpm.

g) Washing

The atelocollagen microcapsules obtained can be washed five times with 1500 ml of the above-mentioned mixture of fatty acid esters —Dragoxat®—and are separated from the suspension under the same conditions as previously. 1.8 kg of microcapsules are obtained; they can be suspended for example in Carbopol® or collagen gels.

As regards use in pharmaceutical compositions, these microcapsules make it possible, when administered orally, to mask the taste of the active principle and to provide protection in the stomach or produce a delayed effect by virtue of resistance to the gastric juices, which can be achieved by appropriate crosslinking.

It is also possible to prepare compositions intended for various methods of administration such as oral and parenteral administration and application to the skin and mucosa.

The present invention further relates, in general terms, to a process for the preparation of a cosmetic, pharmaceutical or food composition, wherein microcapsules with a mixed wall of crosslinked atelocollagen and polyholosides, for example glycosaminoglycans, are incorporated, at least in part, a substance of interest in cosmetics, pharmaceuticals or food preferably having been encapsulated, at least in part, in the said microcapsules.

These microcapsules also make it possible to protect delicate substances, such as essential oils, which may form part of the composition of foods.

Other uses of these microcapsules will be clearly apparent to those skilled in the art.

What is claimed is:

1. A process for the manufacture of microcapsules, which comprises the following successive steps:

(a) preparing a solution of atelocollagen, (b) preparing a solution of polyholoside by dissolving the polyholoside in an aqueous buffer solution whose pH is adjusted so that, after mixing with the solution of atelocollagen, the pH of the mixture is between 5.5 and 10, (c) mixing the solution of atelocollagen with the solution of polyholoside to form a homogeneous solution of atelocollagen and polyholoside having a pH between 5.5 and 10, (d) forming an emulsion with the solution of atelocollagen and polyholoside, as a dispersed phase in a hydrophobic liquid forming the continuous phase, in which the atelocollagen and the polyholoside are essentially insoluble, and (e) mixing a crosslinking solution of a crosslinking agent containing reactive groups capable of simultaneously reacting with acylatable groups of the atelocollagen and the polyholoside with the resulting emulsion, thereby causing an interfacial and simultaneous crosslinking reaction of the atelocollagen and of the polyholoside, for a period of time sufficient to form microcapsules comprising a crosslinked outerwall surrounding a filled inner space, said outerwall resulting from a crosslinking between molecules of atelocollagen and polyholoside.

2. The process of claim 1, wherein the crosslinking agent is selected from the group consisting of an acid dichloride, an acid anhydride, and a dibasic or polybasic carboxylic acid.

3. A process according to claim 2, wherein the crosslinking agent is selected from the group consisting of terephthaloyl chloride, phthaloyl chloride, sebacoyl chloride, succinoyl chloride, and an acid anhydride.

4. A process according to claim 1, wherein said buffer solution is selected from the group consisting of an aqueous solution of sodium hydroxide and an aqueous solution of a buffer having a pH ranging between 7 and 10 obtained by the neutralization of a weak acid with a strong base.

5. A process according to claim 1, wherein the concentration of polyholoside relative to the concentration of atelocollagen ranges between 15 and 50% by weight.

6. A process according to claim 1, wherein the polyholoside is selected from the group consisting of a structural glycosaminoglycan, chondroitin 4-sulfate, chondroitin 6-sulfate, dermatan sulfate, heparin sulfate, keratan sulfate, heparin, low molecular weight heparin having a molecular weight ranging from about 2000–10000, and a dextran.

7. A process according to claim 1, wherein at least one active substance selected from the group consisting of a cosmetic a pharmaceutical substance and a food substance is mixed with the aqueous solution of atelocollagen and polyholoside.

8. A process for the manufacture of microcapsules containing a water-immiscible oil, which comprises the following successive steps:

(a) preparing a solution of atelocollagen, (b) preparing a solution of polyholoside by dissolving the polyholoside in an aqueous buffer solution whose pH is adjusted so that, after mixing with the solution of atelocollagen, the pH of the mixture is between 5.5 and 10, (c) mixing the solution of atelocollagen with the solution of polyholoside to form a homogeneous solution of atelocollagen and polyholoside having a pH between 5.5 and 10, (d) forming an emulsion of an oily phase containing said water-immiscible oil and a crosslinking agent as dispersed phase in the solution of atelocollagen and polyholoside forming a continuous phase, (e) agitating the emulsion for a period of time sufficient to form microcapsules comprising a cross-linked outerwall surrounding a filled inner space, said outerwall resulting from crosslinking between molecules of atelocollagen and polyholoside, and (f) recovering the microcapsules.

9. The process of claim 8, wherein the crosslinking agent is selected from the group consisting of an acid dichloride, an acid anhydride, and a dibasic or polybasic carboxylic acid.

10. A process according to claim 8, wherein said hydrophobic liquid in which the atelocollagen and the polyholoside are insoluble is selected from the group consisting of cyclohexane and chloroform.

11. A process according to claim 8, wherein said buffer solution is selected from the group consisting of an aqueous solution of sodium hydroxide and an aqueous solution of a buffer having a pH ranging between 7 and 10 obtained by the neutralization of a weak acid with a strong base.

12. A process according to claim 8, wherein the concentration of polyholoside relative to the concentration of atelocollagen ranges between 15 and 50% by weight.

13. A process according to claim 8, wherein at least one active substance selected from the group consisting of a cosmetic, a pharmaceutical substance and a food substance is mixed with the aqueous solution of atelocollagen and polyholoside.

14. The process according to claim 8, wherein at least one active substance selected from the group consisting of a cosmetic, a pharmaceutical substance and a food substance is mixed with the dispersed oily phase to be encapsulated.

15. A process for the manufacture of microcapsules which comprises the following successive steps:

(a) preparing a solution of atelocollagen, (b) preparing a solution of polyholoside by dissolving the polyholoside in an aqueous buffer solution whose pH is adjusted so that, after mixing with the solution of atelocollagen, the pH of the mixture is between 5.5 and 10, (c) mixing the solution of atelocollagen with the solution of polyholoside to form a homogeneous solution of atelocollagen and polyholoside having a pH between 5.5 and 10, (d) preparing a crosslinking solution containing a crosslinking agent, (e) effecting a laminar extrusion of the homogeneous solution of atelocollagen and polyholoside through an extrusion nozzle, the laminar flow being subjected at the same time to vibrations in order to break up the laminar flow into individual droplets, (f) causing the individual droplets to fall into said crosslinking solution, thereby forming microcapsules comprising a cross-linked outerwall surrounding a filled inner space, said outerwall resulting from crosslinking between molecules of atelocollagen and polyholoside, and (g) recovering the microcapsules.

16. The process of claim 15, wherein the crosslinking agent is selected from the group consisting of an acid dichloride, an acid anhydride, and a dibasic or polybasic carboxylic acid.

17. A process according to claim 15, wherein said buffer solution is selected from the group consisting of an aqueous solution of sodium hydroxide and an aqueous solution of a buffer having a pH ranging between 7 and 10 obtained by the neutralization of a weak acid with a strong base.

18. A process according to claim 15, wherein the concentration of polyholoside relative to the concentration of atelocollagen ranges between 15 and 50% by weight.

19. A process according to claim 15, wherein at least one active substance selected from the group consisting of a cosmetic, a pharmaceutical substance and a food substance is mixed with the aqueous solution of atelocollagen and polyholoside.

20. A process for the manufacture of microcapsules encapsulating an oily phase, which comprises the following successive steps:

(a) preparing a solution of atelocollagen, (b) preparing a solution of polyholoside by dissolving the polyholoside in an aqueous buffer solution whose pH is adjusted so that, after mixing with the solution of atelocollagen, the pH of the mixture is between 5.5 and 10, (c) mixing the solution of atelocollagen with the solution of polyholoside to form a homogeneous solution of atelocollagen and polyholoside having a pH between 5.5 and 10, (d) preparing a crosslinking solution containing a crosslinking agent dissolved in the oily phase to be encapsulated, (e) effecting a laminar coextrusion of the homogeneous solution of atelocollagen and polyholoside and the oily phase to be encapsulated through an extrusion nozzle wherein the oily phase is internally located with regard to the solution of atelocollagen and polyholoside, the laminar flow being subjected at the same time to vibrations in order to break up the laminar flow into individual droplets, (f) causing the individual droplets to fall into a stirred water bath, and (g) recovering the microcapsules.

21. The process of claim 20, wherein the crosslinking agent is selected from the group consisting of an acid dichloride, an acid anhydride, and a dibasic or polybasic carboxylic acid.

22. A process according to claim 20, wherein said buffer solution is selected from the group consisting of an aqueous solution of sodium hydroxide and an aqueous solution of a buffer having a pH ranging between 7 and 10 obtained by the neutralization of a weak acid with a strong base.

23. A process according to claim 20, wherein the concentration of polyholoside relative to the concentration of atelocollagen ranges between 15 and 50% by weight.

24. A process according to claim 20, wherein at least one active substance selected from the group consisting of a cosmetic, a pharmaceutical substance and a food substance is mixed with the aqueous solution of atelocollagen and polyholoside.

25. A process according to claim 20, wherein at least one active substance selected from the group consisting of a cosmetic, a pharmaceutical substance and a food substance is co-extruded inside the laminar flow of atelocollagen and polyholoside which are to form the wall of the microcapsules.

* * * * *